United States Patent
Lee (10) Patent No.: US 9,561,018 B2
(45) Date of Patent: Feb. 7, 2017

(54) METHOD AND APPARATUS FOR GENERATING DIAGNOSIS IMAGE, PROBE, AND METHOD OF CONTROLLING THE PROBE

(71) Applicant: SAMSUNG MEDISON CO., LTD., Gangwon-Do (KR)

(72) Inventor: Kang-Chang Lee, Gangwon-do (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 898 days.

(21) Appl. No.: 13/622,670

(22) Filed: Sep. 19, 2012

(65) Prior Publication Data
US 2013/0072800 A1    Mar. 21, 2013

(30) Foreign Application Priority Data
Sep. 19, 2011 (KR) .................. 10-2011-0094281

(51) Int. Cl.
*A61B 8/00* (2006.01)
*A61B 8/08* (2006.01)

(52) U.S. Cl.
CPC ............... *A61B 8/4477* (2013.01); *A61B 8/54* (2013.01); *A61B 8/56* (2013.01); *A61B 8/585* (2013.01); *A61B 8/08* (2013.01); *A61B 8/4405* (2013.01); *A61B 8/4433* (2013.01); *A61B 8/469* (2013.01); *A61B 8/486* (2013.01); *A61B 8/488* (2013.01)

(58) Field of Classification Search
USPC ........................................ 600/407, 437, 459
See application file for complete search history.

(56) References Cited

U.S. PATENT DOCUMENTS

| | | | |
|---|---|---|---|
| 5,318,027 A * | 6/1994 | Fukui | 600/437 |
| 2006/0173346 A1* | 8/2006 | Lee | 600/459 |
| 2007/0266791 A1 | 11/2007 | Nakamura | |
| 2009/0043203 A1 | 2/2009 | Pelissier et al. | |
| 2009/0275837 A1 | 11/2009 | Shiina et al. | |
| 2010/0191120 A1 | 7/2010 | Kraus et al. | |
| 2010/0191121 A1* | 7/2010 | Satoh | A61B 8/00 600/459 |
| 2010/0292577 A1* | 11/2010 | Sato et al. | 600/459 |

FOREIGN PATENT DOCUMENTS

| | | |
|---|---|---|
| DE | 101 64 758 A1 | 5/2004 |
| EP | 1 676 530 A1 | 7/2006 |

(Continued)

OTHER PUBLICATIONS

Korean Notice of Allowance, w/ English translation thereof, issued in Korean Patent Application No. KR 10-2011-0094281 dated Apr. 29, 2013.

(Continued)

*Primary Examiner* — Joel F Brutus
(74) *Attorney, Agent, or Firm* — McDermott Will & Emery LLP (57) ABSTRACT

A diagnosis image generating apparatus including a plurality of probes, the diagnosis image generating apparatus including at least one element included in each of the plurality of probes; a selecting unit which selects a probe from among the plurality of probes; and a diagnosis image generating unit which generates a diagnosis image of the object by using the selected probe.

15 Claims, 7 Drawing Sheets

(56) References Cited

FOREIGN PATENT DOCUMENTS

| | | |
|---|---|---|
| JP | 2003-135459 A | 5/2003 |
| JP | 2009-268622 A | 11/2009 |
| JP | 2010-220875 A | 10/2010 |
| KR | 2006-0075733 A | 7/2006 |
| KR | 10-2007-0022291 A | 2/2007 |

OTHER PUBLICATIONS

Korean Office Action dated Oct. 23, 2012 from Korean Patent Application No. 10-2011-0094281.
European Search Report dated Nov. 27, 2012 from European Patent Application No. 12183676.1.

\* cited by examiner

METHOD AND APPARATUS FOR GENERATING DIAGNOSIS IMAGE, PROBE, AND METHOD OF CONTROLLING THE PROBE

CROSS-REFERENCE TO RELATED PATENT APPLICATION

This application claims the benefit of Korean Patent Application No. 10-2011-0094281, filed on Sep. 19, 2011, in the Korean Intellectual Property Office, the disclosure of which is incorporated herein in its entirety by reference.

BACKGROUND OF THE INVENTION

1. Field of the Invention

The present invention relates to an apparatus for generating a diagnosis image, a probe, a method of controlling the probe, and a method of generating a diagnosis image.

2. Description of the Related Art

A diagnosis image generating apparatus transmits and receives ultrasound signals via a probe. Here, a probe may receive ultrasound signals by using a piezo element. A diagnosis image generating apparatus may include a plurality of probes. Here, if a user desires to use one of the plurality of probes, the user inputs selection information for selecting one of the plurality of probes by operating the diagnosis image generating apparatus.

SUMMARY OF THE INVENTION

The present invention provides a diagnosis image generating apparatus and a probe with improved convenience, a method of controlling the probe, and a method of generating a diagnosis image.

The present invention also provides a non-transitory computer readable recording medium having recorded thereon a computer program for implementing the method on a computer.

According to an aspect of the present invention, there is provided a diagnosis image generating apparatus including a plurality of probes, the diagnosis image generating apparatus including at least one element which is included in each of the plurality of probes, transmits a signal, and receives an echo signal; a detecting unit which detects information regarding an object from echo signals received by the plurality of probes; a selecting unit which selects a probe by which receives the echo signal from which information regarding the object is detected from among the plurality of probes; and a diagnosis image generating unit which generates a diagnosis image of the object by using the selected probe.

According to another aspect of the present invention, there is provided a probe including at least one element which transmits a signal and receives an echo signal; a detecting unit which detects information regarding an object from the echo signal; and a control unit which activates or deactivates the probe.

According to another aspect of the present invention, there is provided a diagnosis image generating apparatus including a plurality of probes, the diagnosis image generating apparatus including a selecting unit which selects a probe currently in use from among the plurality of probes by analyzing frequency spectrums of echo signals received by the plurality of probes; and a diagnosis image generating unit which generates a diagnosis image of the object by using the selected probe.

According to another aspect of the present invention, there is provided a method of generating a diagnosis image by using a diagnosis image generating apparatus including a plurality of probes, the method including transmitting a signal from each of the plurality of probes; receiving an echo signal, at each of the plurality of probes; detecting information regarding an object from the received echo signals; selecting a probe at which receives the echo signal from which information regarding the object is detected from among the plurality of probes; and generating a diagnosis image of the object by using the selected probe.

According to another aspect of the present invention, there is provided a method of controlling a probe, the method including receiving an echo signal by at least one element included in the probe; detecting information regarding an object from the received echo signal; and activating or deactivating the probe based on a result of the detection.

According to another aspect of the present invention, there is provided a method of generating a diagnosis image by using a probe from among a plurality of probes, the method including selecting a probe whose contact is detected by a contact sensor included in each of the plurality of probes, from among the plurality of probes; and generating a diagnosis image of an object by using the selected probe.

According to another aspect of the present invention, there is provided a non-transitory computer readable recording medium having recorded thereon a computer program for implementing any of the methods above.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Expressions such as "at least one of," when preceding a list of elements, modify the entire list of elements and do not modify the individual elements of the list.

Hereinafter, the present invention will be described in detail by explaining preferred embodiments of the invention with reference to the attached drawings.

Figure 1:
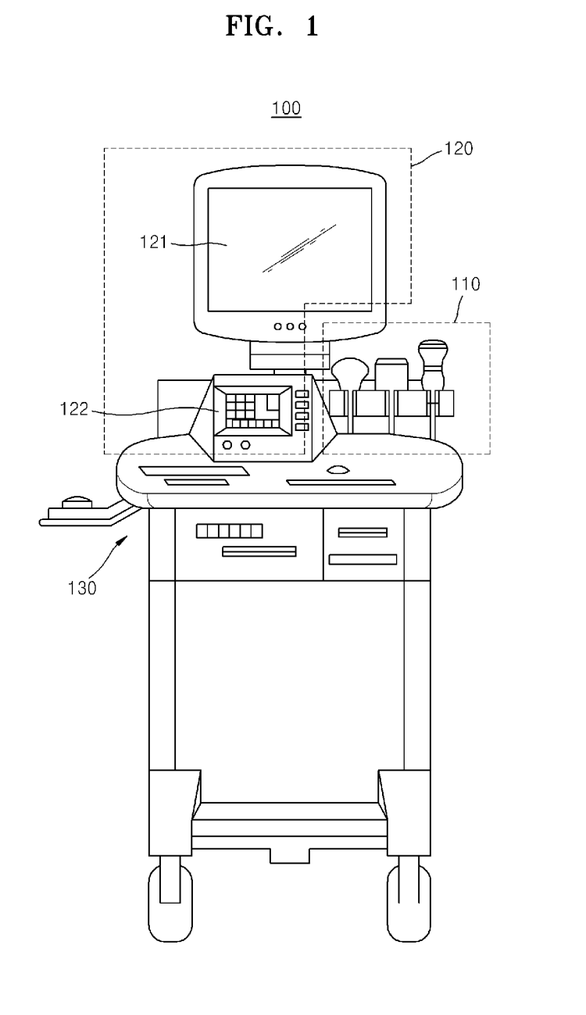
FIG. 1 is a diagram showing a diagnosis image generating apparatus according to an embodiment of the present invention.

FIG. 1 is a diagram showing a diagnosis image generating apparatus 100 according to an embodiment of the present invention. Referring to FIG. 1, the diagnosis image generating apparatus 100 according to the present embodiment includes a plurality of probes 110, a user interface (UI) unit 120, and a main system 130.

The diagnosis image generating apparatus 100 shown in FIG. 1 includes only components related to the present embodiment. Therefore, one of ordinary skill in the art will understand that the diagnosis image generating apparatus 100 may further include other general components other than the components shown in FIG. 1.

Referring to FIG. 1, the diagnosis image generating apparatus 100 is an apparatus for generating diagnosis images of an object. However, the present invention is not limited thereto, and the diagnosis image generating apparatus 100 may further include functions, such as displaying generated diagnosis images or outputting generated diagnosis images to an external apparatus (not shown). Furthermore, the diagnosis image generating apparatus 100 may be an apparatus for transmitting ultrasound signals to an object and generating ultrasound images by using echo signals reflected by the object. However, the present invention is not limited thereto.

The plurality of probes 110 transmit ultrasound signals to an object and receive echo signals reflected by the object. Although three probes are employed in the present embodiment, the present invention is not limited thereto, and the diagnosis image generating apparatus 100 may include at least two probes.

As shown in FIG. 1, when the plurality of probes 110 are not in use, the plurality of probes 110 may be fixed to a mounting unit formed on the diagnosis image generating apparatus 100. In this case, a user may use a probe from among the plurality of probes 110 for generating a diagnosis image of an object.

Each of the plurality of probes 110 includes at least one element. An element according to the present embodiment may be a transducer for converting electric signals to ultrasound signals and vice versa. However, the present invention is not limited thereto.

Furthermore, each of the plurality of probes 110 may further include a detecting unit (not shown) for detecting information regarding an object from received echo signals and a control unit (not shown) for activating or deactivating the probe based on a result of the detection. Detailed descriptions thereof will be given below with reference to FIG. 2.

Each of the plurality of probes 110 transmits signals to an object and receives echo signals reflected by the object via at least one element.

The UI unit 120 obtains input information input by a user and displays output information to the user. The UI unit 120 according to the present embodiment may include a display unit 121 and an input unit 122. However, the present invention is not limited thereto, and the UI unit 120 may be embodied as a unit having an input and output function.

For example, the UI unit 120 according to the present embodiment may include input/output devices, such as a keyboard, a mouse, a monitor, a touch panel, or a speaker, and software for operating the same. However, the present invention is not limited thereto.

The main system 130 controls the overall operation of the diagnosis image generating apparatus 100. In other words, the main system 130 controls the plurality of probes 110 and the UI unit 120.

Furthermore, the main system 130 according to the present embodiment may further include a detecting unit (not shown) which detects information regarding an object from echo signals respectively received by the plurality of probes 110, a selecting unit (not shown) for selecting one from among the plurality of probes 110, and a diagnosis image generating unit (not shown) which generates a diagnosis image of the object by using a selected probe. Detailed descriptions thereof will be given below with reference to FIG. 3.

Accordingly, the diagnosis image generating apparatus 100 according to the present embodiment may generate a diagnosis image of an object by using one from among the plurality of probes 110.

Figure 2:
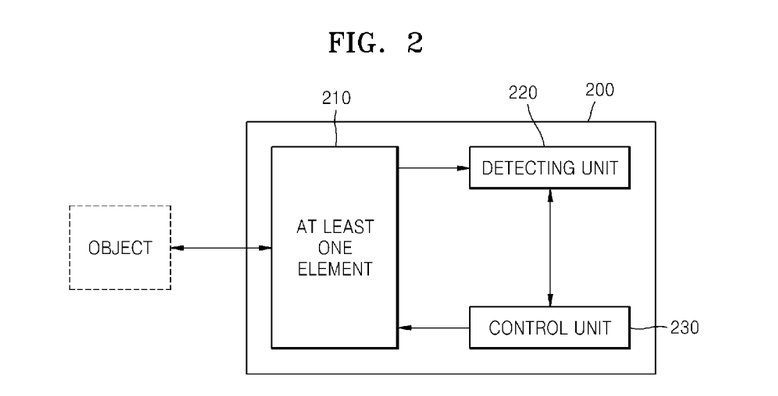
FIG. 2 is a diagram showing a probe from among the plurality of probes 110 shown in FIG. 1.

FIG. 2 is a diagram showing a probe 200 from among the plurality of probes 110 shown in FIG. 1. Referring to FIG. 2, the probe 200 includes at least one element 210, a detecting unit 220, and a control unit 230.

The probe 200 shown in FIG. 2 includes only components related to the present embodiment. Therefore, one of ordinary skill in the art will understand that the probe 200 may further include other general components other than the components shown in FIG. 2.

Furthermore, since the probe 200 is an example of the plurality of probes 110, descriptions given above with reference to FIG. 1 may also be applied to the probe 200 shown in FIG. 2. Therefore, repeated descriptions will be omitted.

The probe 200 transmits signals to an object and receives echo signals reflected by the object by using the at least one element 210.

The at least one element 210 may be one element, p elements, or p×q elements. As described above, the element according to the present embodiment may be a transducer. However, the present invention is not limited thereto. Here, p and q may be natural numbers equal to or greater than 1.

Therefore, the at least one element 210 transmits signals and receives echo signals. For example, the echo signals may be a reflection signal corresponding to the signal transmitted by the at least one element 210. Here, the at least one element 210 according to the present embodiment may transmit signals and receive echo signals by using only one element. Thus, only one element 210 may be used to transmit signals and receive echo signals.

For example, the probe 200 according to the present embodiment may automatically determine whether the probe 200 is in use and may automatically be activated or deactivated. Therefore, the probe 200 may transmit signals and receive echo signals by using only one element to determine whether the probe 200 is in use.

Therefore, the probe 200 according to the present embodiment does not perform beamformating with respect to received echo signals and only determines whether the received echo signals include information regarding an object. Therefore, an amount of calculation to be performed by the probe 200 may not increase.

The detecting unit 220 detects information regarding an object from echo signals received by the at least one element 210. For example, the detecting unit 220 may detect information regarding an object by analyzing frequency spectrums of echo signals.

A case in which the probe 200 is in use will be described below in more detail. Here, the expression "the probe 200 is in use" indicates a case in which a user of the probe 200 contacts the probe 200 to an object or brings the probe 200 close to the object. However, definition of the expression is not limited thereto.

When the probe 200 is in use, a signal transmitted by the at least one element 210 reaches an object, and thus an echo signal received by the at least one element 210 may be a signal reflected by the object. Therefore, an echo signal received by the at least one element 210 includes information regarding the object and the information regarding the object may be detected by analyzing frequency spectrums of the echo signal.

A case in which the probe 200 is not in use will be described below in more detail. Here, the expression "the probe 200 is not in use" indicates a case in which the probe 200 is not contacting an object or is not close to the object and is fixed to a mounting unit for the probe 200. However, definition of the expression is not limited thereto.

When the probe 200 is not in use, a signal transmitted by the at least one element 210 does not reach an object. According to environments, a signal transmitted by the at least one element 210 may reach an arbitrary object, not a target object, that is far away or may disappear in the air. Therefore, an echo signal received by the at least one element 210 barely includes information regarding the object and the absence of information regarding the object may be detected by analyzing frequency spectrums of the echo signal.

The control unit 230 activates or deactivates the probe 200 based on a result of the detection by the detecting unit 220. For example, the control unit 230 activates the probe 200 if information regarding an object is detected from an echo signal received by the probe 200 and deactivates the probe 200 if information regarding an object is not detected from an echo signal received by the probe 200.

Here, the activation of the probe 200 means continuous transmission and reception of signals by the at least one element 210, whereas deactivation of the probe 200 means no more transmission and reception of signals by the at least one element 210.

Furthermore, while the probe 200 is activated, the control unit 230 deactivates the probe 200 if information regarding an object is not detected from an echo signal received by the probe 200.

For example, when a user performs diagnosis with respect to an object by using the probe 200, the probe 200 may be converted from the state of in use into the state of not in use after the diagnosis is completed.

Therefore, even when the probe 200 is activated, the detecting unit 220 according to the present embodiment continuously detects information regarding an object from echo signals received by the probe 200, and the control unit 230 deactivates the probe 200 if information regarding the object is not detected any more from the echo signals received by the probe 200.

Therefore, since the probe 200 is automatically activated or deactivated based on whether the probe 200 is in use, a user may use the probe 200 without manipulating the probe 200 to turn the probe 200 on or off.

Furthermore, since it may be determined whether the probe 200 is in use by using signals transmitted and received by only one of elements included in the probe 200, it may be determined whether the probe 200 is in use without increasing the amount of calculations or using additional hardware, e.g., an additional sensor.

However, the present invention is not limited thereto. For example the probe 200 according to the present embodiment may include a contact sensor (not shown) and may determine whether the probe 200 is in use by using the contact sensor.

Therefore, a selecting unit 134 according to the present embodiment selects a probe whose contact is detected by a contact sensor included in each of the plurality of probes 110, from among the plurality of probes 110, and the diagnosis image generating unit 136 may generate a diagnosis image of an object by using the probe selected by the selecting unit 134.

However, the selecting unit 134 may select a contacted probe from among the plurality of probes 110 based on information input by a user. For example, if contact sensors of two or more probes from among the plurality of probes 110 detect contacts, the selecting unit 134 may select one of the contacting probes based on selection information input by a user via an input unit (not shown).

Therefore, a diagnosis image may be conveniently generated by using one from among the plurality of probes 110.

Although FIG. 2 shows that the probe 200 includes the detecting unit 220 and the control unit 230 for convenience of explanation, the detecting unit 220 and the control unit 230 according to the present embodiment may be included in the main system 130 of the diagnosis image generating apparatus 100 shown in FIG. 1. In this case, the probe 200 according to the present embodiment may not perform functions of the detecting unit 220 and the control unit 230.

Figure 3:
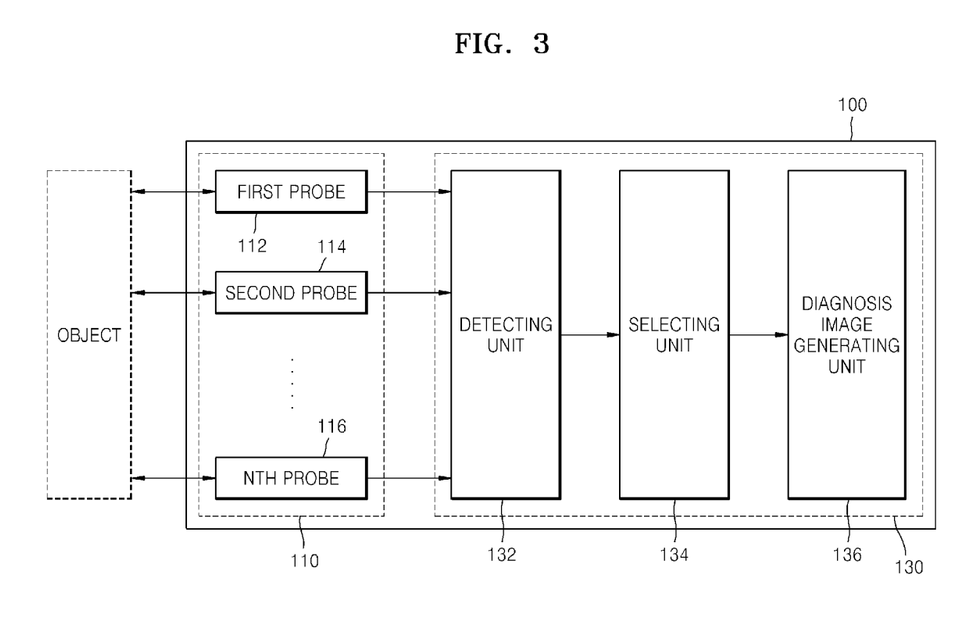
FIG. 3 is a diagram showing another example of the diagnosis image generating apparatus shown in FIG. 1.

FIG. 3 is a diagram showing another example of the diagnosis image generating apparatus 100 shown in FIG. 1. Referring to FIG. 3, the diagnosis image generating apparatus 100 includes the plurality of probes 110 and the main system 130. The plurality of probes 110 includes a first probe 112, a second probe 114, and an $N^{th}$ probe 116. The main system 130 includes a detecting unit 132, the selecting unit 134, and the diagnosis image generating unit 136. Here, N may be 3 or a greater natural number.

The diagnosis image generating apparatus 100 shown in FIG. 3 includes only components related to the present embodiment. Therefore, one of ordinary skill in the art will understand that the diagnosis image generating apparatus 100 may further include other general components other than the components shown in FIG. 3.

Since the first probe 112, the second probe 114, and the $N^{th}$ probe 116 shown in FIG. 3 are examples of the probe 200 shown in FIG. 2, any description of the probe 200 given above in relation to FIG. 2 may also be applied to the first probe 112, the second probe 114, and the $N^{th}$ probe 116 shown in FIG. 3, and thus repeated descriptions will be omitted.

Furthermore, the diagnosis image generating apparatus 100 shown in FIG. 3 is another example of the diagnosis image generating apparatus 100 shown in FIG. 1. Therefore, the components of the diagnosis image generating apparatus 100 according to the present embodiment are not limited to those shown in FIG. 1 or FIG. 3. Furthermore, any description of the diagnosis image generating apparatus 100 given above in relation to FIG. 1 may also be applied to the diagnosis image generating apparatus 100 shown in FIG. 3, and thus repeated descriptions will be omitted.

Each of the first probe 112, the second probe 114, and the $N^{th}$ probe 116 transmits a signal and receives an echo signal, by using at least one element. For example, at least one element included in each the first probe 112, the second probe 114, and the $N^{th}$ probe 116 transmits a signal and receives an echo signal.

Here, each of the first probe 112, the second probe 114, and the $N^{th}$ probe 116 may transmit a signal and receive an echo signal by using only one element. Therefore, the amount of calculations to be performed by the diagnosis image generating apparatus 100 will not increase.

The detecting unit 132 detects information regarding an object from echo signal received by each of the plurality of probes 110. For example, the detecting unit 132 detects information regarding an object from echo signal received by each of the first probe 112, the second probe 114, and the $N^{th}$ probe 116. Here, the detecting unit 132 may detect information regarding the object by analyzing frequency spectrums of the echo signals.

From among the plurality of probes 110, the selecting unit 134 selects a probe by which receives an echo signal from which information regarding the object is detected. In other words, the selecting unit 134 selects a probe currently in use from among the plurality of probes 110. Here, the probe currently in use may correspond to a probe that is contacting or close to the object. However, the present invention is not limited thereto.

For example, if information regarding the object is detected from an echo signal received by the first probe 112 and no information regarding the object is detected from echo signals received by the second probe 114 and the Nth probe 116, the selecting unit 134 selects the first probe 112.

The diagnosis image generating unit 136 generates a diagnosis image of the object by using a probe selected by the selecting unit 134. For example, the diagnosis image generating unit 136 may include a digital signal processor (DSP) (not shown) and a digital scan converter (DSC) (not shown). The DSP according to the present embodiment forms image data for displaying b-mode(brightness mode), c-mode(color mode), or d-mode(doppler mode) by using signals received by the probe selected by the selecting unit 134, and the DSC generates a diagnosis image scan-converted to display the image data formed by the DSP.

Furthermore, the diagnosis image generating unit 136 according to the present embodiment may generate a diagnosis image of an object based on selection information input by a user. For example, selection information input by a user may include information indicating a body part corresponding to an object and information regarding a resolution and size of a diagnosis image. However, the present invention is not limited thereto.

Therefore, the diagnosis image generating apparatus 100 may automatically generate a diagnosis image by using a probe currently in use from among the plurality of probes 110.

Figure 4:
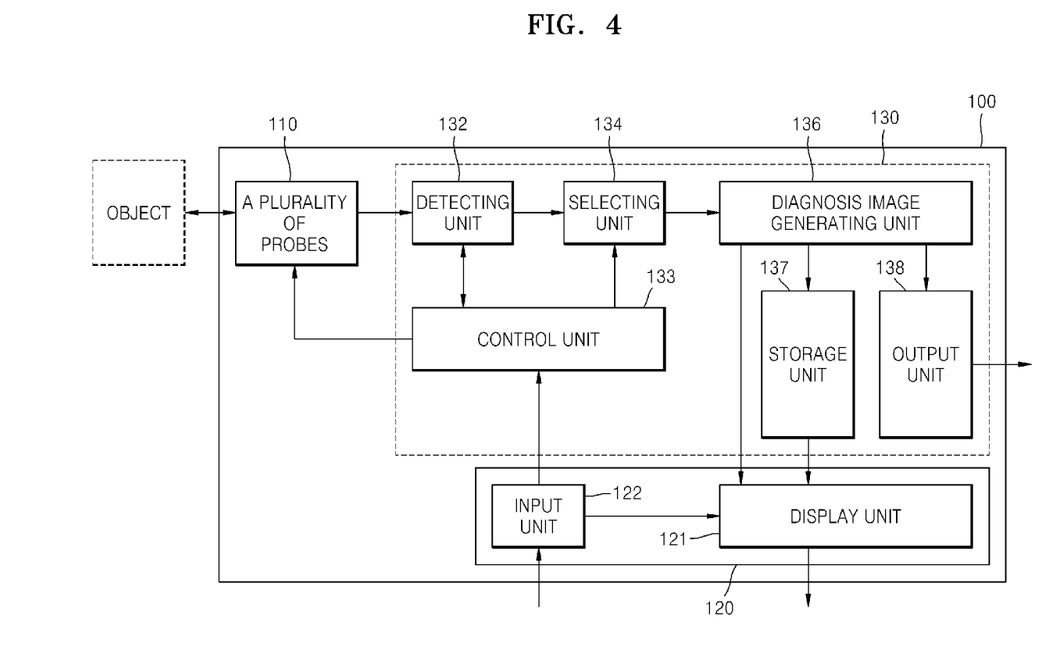
FIG. 4 is a diagram showing another example of the diagnosis image generating apparatus shown in FIG. 1.

FIG. 4 is a diagram showing another example of the diagnosis image generating apparatus 100 shown in FIG. 1. Referring to FIG. 4, the diagnosis image generating apparatus 100 includes the plurality of probes 110, the UI unit 120, and the main system 130. The UI unit 120 includes a display unit 121 and an input unit 122. The main system 130 includes the detecting unit 132, a control unit 133, the selecting unit 134, the diagnosis image generating unit 136, a storage unit 137, and an output unit 138.

The diagnosis image generating apparatus 100 shown in FIG. 4 includes only components related to the present embodiment. Therefore, one of ordinary skill in the art will understand that the diagnosis image generating apparatus 100 may further include other general components other than the components shown in FIG. 4.

Furthermore, the diagnosis image generating apparatus 100 shown in FIG. 4 is another example of the diagnosis image generating apparatus 100 shown in FIGS. 1 and 3. Therefore, the components of the diagnosis image generating apparatus 100 according to the present embodiment are not limited to those shown in FIG. 4. Furthermore, any description of the diagnosis image generating apparatus 100 given above in relation to FIGS. 1 and 3 may also be applied to the diagnosis image generating apparatus 100 shown in FIG. 4, and thus repeated descriptions will be omitted.

Each of the plurality of probes 110 transmits a signal and receives an echo signal by using at least one element included in each of the plurality of probes 110.

The UI unit 120 receives information from a user and displays output information to the user.

For example, the UI unit 120 may include the display unit 121 for displaying output information to a user and the input unit 122 for receiving information from the user. However, the present invention is not limited thereto, and the UI unit 120 may be embodied as a single unit which functions as both the display unit 121 and the input unit 122.

Furthermore, the display unit 121 according to the present embodiment may display a selection menu for receiving selection information from a user, and the input unit 122 may receive selection information from a user for selecting an item in the selection menu.

The display unit 121 may display a selection menu including body parts corresponding to objects, and the input unit 122 may receive selection information for selecting an item in the selection menu.

For example, the display unit 121 may display a selection menu including liver, stomach, fetus, heart, etc., and the input unit 122 may receive selection information for selecting an item in the selection menu.

Alternatively, the display unit 121 may display a selection menu including at least one of a resolution and size of a diagnosis image, and the input unit 122 may receive selection information from a user for selecting an item in the selection menu.

The display of a selection menu and reception of selection information according to the present embodiment may be performed after a probe is selected by the selecting unit 134. However, the present invention is not limited thereto. Accordingly, the diagnosis image generating unit 136 may generate a diagnosis image of an object based on selection information from a user.

Furthermore, the control unit 133 may control a probe selected by the selecting unit 134 based on selection information input by a user. For example, a probe selected by the selecting unit 134 may transmit and receive signals to and from an object based on information of the object according to selection information of a user.

The main system 130 controls the overall operations of the diagnosis image generating apparatus 100.

The detecting unit 132 detects information regarding an object from echo signals received by each of the plurality of probes 110.

Based on a result of the detection by the detecting unit 132, the control unit 133 activates or deactivates each of the plurality of the probes 110. Furthermore, if no information regarding an object is detected any more from an echo signal selected by the selecting unit 134, the control unit 133 deactivates the selected probe.

Here, the control unit 133 may transmit a control result of activating or deactivating a probe to the selecting unit 134, and the selecting unit 134 may determine that an activated probe is either a probe that is in use or a probe from which information regarding an object may be detected.

A case in which the plurality of probes 110 include a first probe and a second probe will now be described. As a result of detection by the detecting unit 132, the control unit 133 activates the first probe and deactivates the second probe from among the plurality of probes 110 if information regarding an object is detected from an echo signal received by the first probe and information regarding an object is not detected from an echo signal received by the second probe.

When the first probe is activated, the selecting unit 134 selects the first probe, and the diagnosis image generating unit 136 generates a diagnosis image of the object by using the first probe. Furthermore, the control unit 133 continuously monitors the first probe selected by the selecting unit 134, and, when no information regarding the object is detected from an echo signal received by the first probe, the control unit 133 may deactivate the first probe.

Accordingly, the diagnosis image generating apparatus 100 according to the present embodiment may generate a diagnosis image of an object by using one of the plurality of probes 110 without user manipulation, and activation of the probe will be automatically terminated when the probe is no longer being used.

The selecting unit 134 selects a probe from among the plurality of probes 110 by which receives an echo signal from which information regarding an object is detected. Alternatively, the selecting unit 134 according to the present embodiment may select an activated probe from among the plurality of probes 110 as a probe that is in use based on a control result from the control unit 133.

The diagnosis image generating unit 136 generates a diagnosis image of an object by using the probe selected by the selecting unit 134, the storage unit 137 stores the diagnosis image generated by the diagnosis image generating unit 136, and the output unit 138 outputs the diagnosis image generated by the diagnosis image generating unit 136 to an external device. Here, the external device may be a medical imaging system, a general-purpose computer system, a mobile terminal, a personal digital assistant (PDA), a universal serial bus (USB) memory, a facsimile machine, etc.

The storage unit 137 according to the present embodiment is a general storage medium, and one of ordinary skill in the art will understand that the storage unit 137 may include a hard disk drive (HDD), a read only memory (ROM), a random access memory (RAM), a flash memory, and a memory card.

The output unit 138 may exchange data with an external device via a wired network, a wireless network, or wired direct communication. Here, the network may include Internet, a local area network (LAN), a wireless LAN, a wide area network (WAN), a personal area network (PAN), etc. However, the present invention is not limited thereto, and the network may be any of various other types of networks via which data may be transmitted and received.

Accordingly, one of ordinary skill in the art will understand that the storage unit 137 and the output unit 138 according to the present embodiment may be embodied as a single unit, such as a picture archiving communication system (PACS) with additional functions, such as image reading and image searching.

As described above, a user manipulate one of the plurality of probes 110 to contact or move close to an object, the diagnosis image generating apparatus 100 may automatically generate a diagnosis image without manipulation for selecting a probe to be used from among the plurality of probes 110.

Furthermore, when a user finishes using a probe that is in use and fixes the probe to the diagnosis image generating apparatus 100, activation of the probe that is in use may be automatically terminated.

Therefore, the diagnosis image generating apparatus 100 according to the present embodiment may have improved user convenience.

Figure 5:
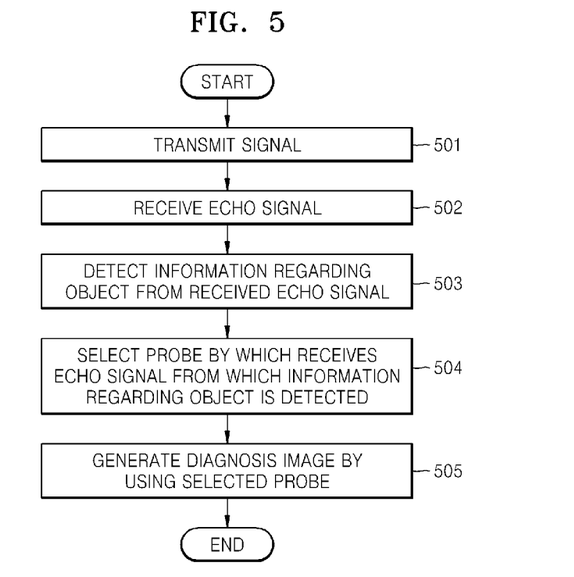
FIG. 5 is a flowchart showing a method of generating a diagnosis image by using the diagnosis image generating apparatus including the plurality of probes, according to an embodiment of the present invention.

FIG. 5 is a flowchart showing a method of generating a diagnosis image by using the diagnosis image generating apparatus 100 including the plurality of probes 110, according to an embodiment of the present invention. Referring to FIG. 5, the method of generating a diagnosis image includes operations that are chronologically performed by the diagnosis image generating apparatus 100 and the probe 200 shown in FIGS. 1 through 4. Therefore, even if omitted below, any of the descriptions given above in relation to the diagnosis image generating apparatus 100 and the probe 200 shown in FIGS. 1 through 4 may be applied to the method of generating a diagnosis image by using the diagnosis image generating apparatus 100 including the plurality of probes 110 as shown in FIG. 5.

In operation 501, each of the plurality of probes 110 transmits a signal. Here, each of the plurality of probes 110 may transmit the signal by using only one element.

In operation 502, each of the plurality of probes 110 receives an echo signal, according to the signal transmitted in operation 501. Here, each of the plurality of probes 110 may receive the echo signal by using only one element.

In operation 503, the detecting unit 132 detects information regarding an object from the echo signal received in operation 502. Here, the detecting unit 132 may detect information regarding the object by analyzing a frequency spectrum of the echo signal.

In operation 504, the selecting unit 134 selects a probe from among the plurality of probes 110 by which receives an echo signal from which information regarding the object is detected.

In operation 505, the diagnosis image generating unit 136 generates a diagnosis image by using the probe selected in operation 504.

Here, operations 501 through 505 may be automatically performed as the diagnosis image generating apparatus 100 is turned on. Therefore, a user may generated a diagnosis image of the object by contacting one of the plurality of probes 110 or bringing it close to the object.

Figure 6:
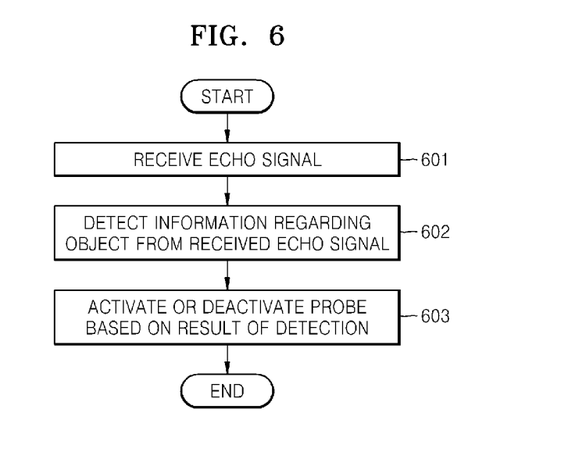
FIG. 6 is a flowchart showing a method of controlling the probe according to the present embodiment.

FIG. 6 is a flowchart showing a method of controlling the probe 200 according to the present embodiment. Referring to FIG. 6, the method of controlling the probe 200 includes operations that are chronologically performed by the probe 200 shown in FIG. 2. Therefore, even if omitted below, any of the descriptions given above in relation to the probe 200 shown in FIG. 2 may be applied to the method of controlling the probe 200 as shown in FIG. 6.

In an operation 601, the at least one element 210 included in the probe 200 receives an echo signal according to a signal transmitted by the at least one element 210. Here, in the operation 601, the echo signal according to the signal transmitted by only an element, may be received.

In operation 602, a detecting unit 620 detects information regarding an object from the echo signal received in the operation 601. Here, the detecting unit 620 detects information regarding the object by analyzing frequency spectrums of the echo signal.

In operation 603, the control unit 630 activates or deactivates the probe 200 based on a result of the detection in operation 602. For example, the control unit 630 activates the probe 200 if information regarding an object is detected from the echo signal received by the probe 200 and deactivates the probe 200 if information regarding an object is not detected from the echo signal received by the probe 200.

Accordingly, in the method of controlling the probe 200 according to the present embodiment, the probe 200 is automatically activated or deactivated based on whether the probe 200 is in use, and thus user convenience may be improved.

Figure 7:
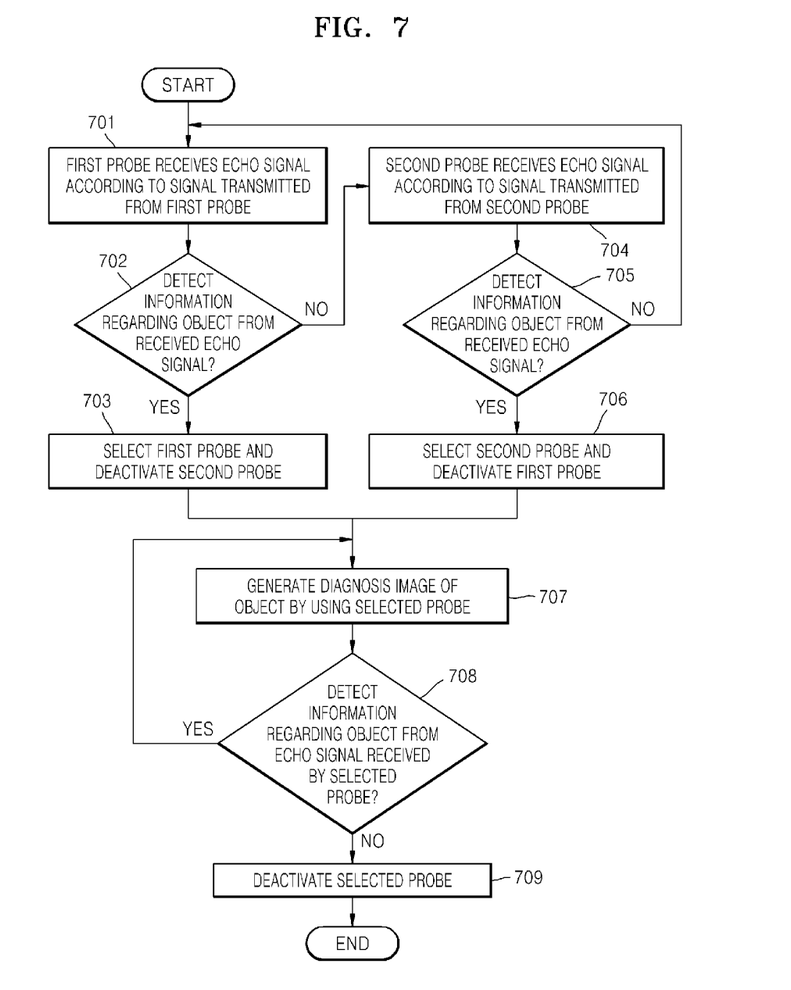
FIG. 7 is a diagram showing a method of generating a diagnosis image by using the diagnosis image generating apparatus including the plurality of probes, according to another embodiment of the present invention.

FIG. 7 is a diagram showing a method of generating a diagnosis image by using the diagnosis image generating apparatus 100 including the plurality of probes 110, according to another embodiment of the present invention. Referring to FIG. 7, the method of generating a diagnosis image includes operations that are chronologically performed by the diagnosis image generating apparatus 100 and the probe 200 shown in FIGS. 1 through 4. Therefore, even if omitted below, any of the descriptions given above in relation to the diagnosis image generating apparatus 100 and the probe 200 shown in FIGS. 1 through 4 may be applied to the method of generating a diagnosis image by using the diagnosis image generating apparatus 100 including the plurality of probes 110 as shown in FIG. 7.

Although only the first probe 112 and the second probe 114 are shown in FIG. 7 for convenience of explanation, the present invention is not limited thereto. The diagnosis image generating apparatus 100 may include the plurality of probes 110.

In operation 701, the first probe 112 receives an echo signal according to a signal transmitted from the first probe 112. In operation 702, the detecting unit 132 detects information regarding an object from the received echo signal. As a result of the detection, if information regarding the object is detected from the echo signal received by the first probe 112, the method proceeds to operation 703. If no information regarding the object is detected from the echo signal received by the first probe 112, the method proceeds to operation 704.

In operation 703, the selecting unit 134 selects the first probe 112, and the control unit 133 deactivates the second probe 114.

In operation 704, the second probe 114 receives an echo signal according to a signal transmitted from the second probe 114. In operation 705, the detecting unit 132 detects information regarding an object from the received echo signal. As a result of the detection, if information regarding the object is detected from the echo signal received by the second probe 114, the method proceeds to operation 706. If no information regarding the object is detected from the echo signal received by the second probe 114, the method returns to operation 701.

In operation 706, the selecting unit 134 selects the second probe 114, and the control unit 133 deactivates the first probe 112.

Here, although FIG. 7 shows that the operations 701 through 704 are performed in the order stated above, the present invention is not limited thereto, and the operations 701 through 704 may be performed simultaneously.

In operation 707, the diagnosis image generating unit 136 generates a diagnosis image of an object by using the selected probe.

In operation 708, the detecting unit 132 detects information regarding an object from an echo signal received by the selected probe. As a result of the detection, if information regarding the object is detected from the echo signal received by the selected probe, the method proceeds to operation 707. If no information regarding the object is detected from the echo signal received by the selected probe, the method proceeds to operation 709.

Here, the operation 708 according to the present embodiment may be simultaneously performed while the diagnosis image generating unit 136 is generating a diagnosis image of the object. For example, the detecting unit 132 may detect information regarding an object from an echo signal received by using only one element or detect information regarding the object from echo signals received for generating a diagnosis image.

In operation 709, the control unit 133 deactivates the selected probe.

As described above, a diagnosis image of an object may be generated by using one from among the plurality of probes 110, and after completion, generation of a diagnosis image may be stopped automatically.

As described above, a user may conveniently generate a diagnosis image by using the diagnosis image generating apparatus 100 and the probe 200 according to the present embodiment without a complicated manipulation for selecting one from among the plurality of probes 110.

Figure 8:
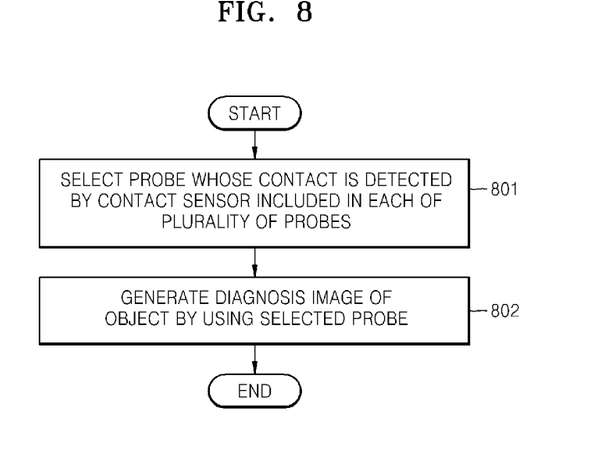
FIG. 8 is a diagram showing a method of generating a diagnosis image by using a probe from among the plurality of probes, according to an embodiment of the present invention.

FIG. 8 is a diagram showing a method of generating a diagnosis image by using a probe from among the plurality of probes 110, according to an embodiment of the present invention. Referring to FIG. 8, the method of generating a diagnosis image includes operations that are chronologically performed by the diagnosis image generating apparatus 100 and the probe 200 shown in FIGS. 1 through 4.

Therefore, even if omitted below, any of the descriptions given above in relation to the diagnosis image generating apparatus 100 and the probe 200 shown in FIGS. 1 through 4 may be applied to the method of generating a diagnosis image by using a probe from among the plurality of probes 110 as shown in FIG. 8.

In operation 801, the selecting unit 134 selects a probe whose contact is detected by a contact sensor included in each of the plurality of probes 110, from among the plurality of probes 110. Here, the selecting unit 134 may select one from among the plurality of probes 110 by receiving a control signal indicating whether a contact is detected from a contact sensor included in each of the plurality of probes 110.

In operation 802, the diagnosis image generating unit 136 generates a diagnosis image of an object by using the probe selected in the operation 801.

Accordingly, a probe currently in use may be conveniently selected from among the plurality of probes 110.

Therefore, as operating times of the diagnosis image generating apparatus 100 and the probe 200 according to the present embodiment are optimized, power consumed by the diagnosis image generating apparatus 100 and the probe 200 may be reduced, and lifespan of the diagnosis image generating apparatus 100 and the probe 200 may be extended.

Diagnosis images generated by using the diagnosis image generating apparatus 100 and the probe 200 according to the present embodiment may not include unnecessary images and may include only images required for diagnosis. In other words, since the diagnosis image generating apparatus 100 and the probe 200 according to the present embodiment may automatically generate a diagnosis image without inputting any instructions for starting and terminating the diagnosis, diagnosis images generated by using the diagnosis image generating apparatus 100 and the probe 200 may not include unnecessary images corresponding to a period of time from input of an instruction for starting the diagnosis to initiation of the diagnosis and a period of time from completion of the diagnosis and input of an instruction for terminating the diagnosis. Therefore, the diagnosis time with respect to the diagnosis image generated by using the diagnosis image generating apparatus 100 and the probe 200 may be reduced.

The present invention may be embodied in a general purpose digital computer by running a program from a computer-readable medium. Data used in the method may be recorded by using various means in a computer-readable recording medium. Examples of the computer-readable medium include storage media such as magnetic storage media (e.g., ROMs, floppy discs, or hard discs), optically readable media (e.g., compact disk-read only memories (CD-ROMs), or digital versatile disks (DVDs)), or PC Interface (e.g., PCI, or PCI-express, Wifi). While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A diagnosis image generating apparatus comprising:
a plurality of probes comprising at least one transducer configured to transmit a signal to an imaging target object and receive an echo signal reflected from the imaging target object;
a detector configured to detect information regarding the imaging target object from the echo signals received by the plurality of probes;
a selector configured to select a probe which receives the echo signal from which information regarding the imaging target object is detected from among the plurality of probes; and
a diagnosis image generator configured to generate a diagnosis image of the imaging target object by using a selected probe,
wherein the selector automatically selects a probe that is contacting or close to the imaging target object from among the plurality of probes.

2. The diagnosis image generating apparatus of claim 1, wherein the at least one transducer transmits the echo signal and receives the echo signal by using only one transducer.

3. The diagnosis image generating apparatus of claim 1, wherein the detector detects the information regarding the imaging target object by analyzing a frequency spectrum of the echo signal.

4. The diagnosis image generating apparatus of claim 1, further comprising a controller configured to deactivate a probe from which no information regarding the imaging target object is detected.

5. The diagnosis image generating apparatus of claim 4, wherein the controller deactivates the selected probe if no information regarding the imaging target object is detected from an echo signal received by the selected probe.

6. A diagnosis image generating apparatus including a plurality of probes, the diagnosis image generating apparatus comprising:
a selector configured to automatically select a probe currently in use from among the plurality of probes by analyzing frequency spectrums of echo signals received by the plurality of probes; and
a diagnosis image generator configured to generate a diagnosis image of an imaging target object by using the automatically selected probe,
wherein the automatically selected probe currently in use is a probe that is contacting or close to the imaging target object.

7. A method of generating a diagnosis image by using a diagnosis image generating apparatus including a plurality of probes, the method comprising:
transmitting a signal to an imaging target object from each of the plurality of probes;
receiving an echo signal reflected from the imaging target object, at each of the plurality of probes;
detecting information regarding the imaging target object from received echo signals;
automatically selecting a probe at which that receives the echo signal from which information regarding the imaging target object is detected from among the plurality of probes; and
generating a diagnosis image of the imaging target object by using the automatically selected probe,
wherein the automatically selecting the probe comprises selecting a probe that is contacting or close to the imaging target object from among the plurality of probes.

8. The method of claim 7, wherein
in the transmitting of the signal, the signal is transmitted by using only one element of each of the plurality of probes, and
in the receiving of the echo signal, the echo signal is received by using only one element of each of the plurality of probes.

9. The method of claim 7, wherein in the detecting of the information, the information regarding the imaging target object is detected by analyzing a frequency spectrum of the echo signal.

10. The method of claim 7, further comprising:
activating a probe that receives the echo signal from which the information regarding the imaging target object is detected; and
deactivating a probe that receives the echo signal from which no information regarding the imaging target object is detected.

11. The method of claim 7, further comprising:
deactivating the automatically selected probe if no information regarding the imaging target object is detected from an echo signal received by the automatically selected probe.

12. A non-transitory computer readable recording medium having recorded thereon a computer program for implementing the method of claim 7 on a computer.

13. A method of generating a diagnosis image by using a probe from among a plurality of probes, the method comprising:
automatically selecting a probe that is contacting or close to an imaging target object based on a signal detected in each of the plurality of probes, from among the plurality of probes; and
generating a diagnosis image of the imaging target object by using the automatically selected probe.

14. The method of claim 13, wherein in the automatically selecting of the probe, the probe is selected at least in part based on selection information input by a user.

15. A non-transitory computer-readable recording medium having recorded thereon a computer program for implementing the method of claim 13 on a computer.

* * * * *